United States Patent [19]

Frampton

[11] 4,012,452

[45] * Mar. 15, 1977

[54] OLEFIN HYDRATION PROCESS

[75] Inventor: Orville D. Frampton, Wyoming, Ohio

[73] Assignee: National Distillers and Chemical Corporation, New York, N.Y.

[ * ] Notice: The portion of the term of this patent subsequent to Nov. 4, 1992, has been disclaimed.

[22] Filed: July 9, 1975

[21] Appl. No.: 594,423

Related U.S. Application Data

[63] Continuation-in-part of Ser. No. 425,437, Dec. 17, 1973, Pat. No. 3,917,721.

[52] U.S. Cl. .............................. 260/641; 252/437; 260/614 A; 260/643 B; 423/335
[51] Int. Cl.$^2$ ....................................... C07C 29/04
[58] Field of Search ................................... 260/641

[56] References Cited

UNITED STATES PATENTS

| | | | |
|---|---|---|---|
| 2,569,092 | 9/1951 | Deering | 260/641 |
| 2,827,500 | 3/1958 | Bloecher et al. | 260/641 |
| 2,960,477 | 11/1960 | Smith et al. | 260/641 |
| 3,340,313 | 9/1967 | Mitsutani | 260/641 |
| 3,367,742 | 2/1968 | Marotta et al. | 423/335 |
| 3,459,678 | 8/1969 | Hagemeyer et al. | 260/641 |
| 3,917,721 | 11/1975 | Frampton | 260/641 |

FOREIGN PATENTS OR APPLICATIONS

| | | | |
|---|---|---|---|
| 2,237,015 | 2/1973 | Germany | 260/641 |

*Primary Examiner*—Joseph E. Evans
*Attorney, Agent, or Firm*—Kenneth D. Tremain

[57] ABSTRACT

An improved olefin hydration process is disclosed and uses as the catalyst, phosphoric acid supported on a particular type of porous silica xerogel which has been treated with steam under particular temperature conditions.

9 Claims, No Drawings

OLEFIN HYDRATION PROCESS

This application is a continuation-in-part of application Ser. No. 425,437 filed Dec. 17, 1973 now U.S. Pat. No. 3,917,721.

BACKGROUND OF THE INVENTION

The use of silica gel as a support for catalysts is well known. The silica gel is a colloidal system of solid character comprised of colloidal particles of a condensation polymerized silicic acid in a hydrated state which forms a coherent structure. It is an assembly of small, impervious, dense, roughly spherical (diameter roughly 100 A) particles in a rather open or loose random packing. The particles are believed to be spherical since the gels are not crystalline. It is believed that the spheres are bonded together by bridges or fillets of the same material. The pore system within the aggregate is formed by the open spaces between the elementary particles and the porous texture, as characterized by the specific surface area, pore volume and pore diameter, depends on the size and the packing of the elementary particles. There are generally two forms of silica gel — xerogel and aerogel.

An aerogel is a gel in which the liquid phase of a gelled silicic acid solution has been replaced by a gaseous phase in such a way as to avoid the shrinkage which would occur if the gel had been dried directly from a liquid. For example, Kistler prepared silica aerogels by replacing most of the water in the gel with alcohol, heating the gel in an autoclave above the critical temperature of the alcohol so that there was no meniscus between the liquid and gas phases, and venting the vapors. In this way, liquid phase was removed without subjecting the gel structure to the compressive forces due to the surface tension of the liquid-gas interface.

Xerogels are prepared by removal of the water by evaporation from an aqueous gelled silicic acid solution. Evaporation of the liquid phase forms menisci in the pores at the surface of the gel so that the surface tension of the liquid exerts a strong compression on the gel mass. The degree to which the gel can be densified depends on the equilibrium between the compression due to the surface tension and the resistance to compression by the gel framework. Compression will increase with smaller pore diameters; resistance to compression depends upon the strength of the gel which increases with higher packing density and more strongly coalesced structures. Thus, gels of high specific surface, made up of extremely small ultimate silica units and formed at low silica concentration, shrink greatly and crack into fragments upon being dried.

Much of the technology of silica gels involves the problem of making a strong hard gel mass which will not shrink or crack upon being dried and which will be suitable as a catalyst base. On the other hand, there has evolved a considerable art in producing extremely light, friable gels which will break down easily into fine powders for use as fillers in plastics, rubber and the like. This type of xerogel is not suitable for fixed bed catalyst supports.

Other solid forms of silica include the crystalline quartz, tridymite and cristabolite, and these are generally not suitable as catalyst supports because, in part, they are non-porous. The same is true of opal, an amorphous form of silica.

Pelleted diatomaceous earth is a naturally occurring form of siliceous material which is sometimes used as a catalyst support because it has a porous structure and is relatively crush-resistant. However, it also contains alumina and iron impurities which may be harmful to many catalytic reactions.

There is a significant amount of technical literature relating to combining a type of hydrothermal treatment of silica gel with its use as a catalyst support. For example, Czarney et al., Przem. Chem. 46 (4), 203–207 (1967), studied the effect of water pressure (a hydrothermal treatment) and suggested the use of these gels to study the influence of pore structure on catalytic properties. German Offen. 2,127,649 teaches preparing macroporous silica gel spheres by heating them in stream and aqueous ammonia for 3 hours at 10 bars and the resulting material is reported to be useful for catalytic processes. French patent 1,585,305 refers to a method for hardening the surfaces of silica gel without degrading its activity or altering its properties using a heat treatment in a lower alcohol vapor with 10% of its volume as water. Schlaffer et al. J. Phys. Chem. 69 (5), 1530–6 (1965), examined with physical changes that occur to silica and alumina gels upon exposure to steam at moderate to high temperatures and found the surface area and pore volume of silica gel to be less stable to prolonged streaming than those of silica-alumina cracking catalysts.

Other technical literature relates to increasing the crushing strength of silica gel by a steam or water treatment. See, e.g., Bodnikov et al. Zh.Prikl.Khim. 38 (10), 2157–65 (1965) and Sultanov, USSR Patent 281,431. A number of other papers deal with the steam treatment of silica gel to alter pore characteristics.

Micropores are here defined as those measurable by the BET nitrogen adsorption method (see Barrett, The Determination of Pore Volume and Area Distributions In Porous Substances, J. Am. Chem. Soc. 73, 373 (1951)) at $P/P_o=0.967$ which corresponds to pore diameter of 600 A. or less. Macropores are here defined as all other pores contributing to the total porosity. In terms of pore volume, total pore volume, measurable by the method of Innes (Analytical Chemistry 28 No. 3 (March 1956)), comprises pore volume due to micropores (measurable by the BET nitrogen adsorption method) plus pore volume due to macropores. The definition is consistent with one given by Innes.

German Offen. 2,237,015 relates to a phosphoric acid hydration catalyst supported on a treated silica gel carrier. The silica gel carrier material is treated with steam or a mixture of steam and nitrogen at a temperature of 200°–350° C., preferably 250°–300° C., and a pressure of 30–1500 psig to obtain a material of increased crushing strength.

I have found, however, that this treatment irreversibly changes the pore structure of the intermediate density xerogel from one in which most of the pore volume is contributed by the desirable micropores into one in which most of the pore volume is contributed by macropores.

Although the German patent teaches that the steam treatment of the silica gel will increase its strength or wear resistance, it is important to note that the crush strength of the gel is not, per se, transferrable to the catalyst. For example, as is demonstrated in Example 1 below, a sample of virgin grade 57 ID silica xerogel has an average crush strength of 8.6 pounds with 0% equal to or less than 2 pounds. Therefore the phosphoric acid impregnated steam treated silica gel catalysts of the German Offen. could be expected to have a crush strength intermediate between the crush strength of the steam treated gel per se and the same catalyst where the gel has not been steam treated, although not necessarily in excess of the average crush strength of the virgin silica gel.

I have now found that by steam treating silica xerogel by a procedure which is different from the German Offen., a xerogel with a pore structure containing a substantial proportion of desirable micropores, yet also of improved crush strength can be obtained and, very surprisingly, the improved crush strength is transferrable to the support catalyst.

Accordingly, it is the object of this invention to provide an improved phosphoric acid olefin hydration catalyst having substantial microporosity, an average crush strength superior to that obtained in the prior art, and which is prepared from silica gel having a substantial portion of its pore volume contributed by micropores. This and other objects of the invention will become apparent to those skilled in the art from the following detailed description.

SUMMARY OF THE INVENTION

This invention relates to an olefin hydration catalyst and more particularly relates to an olefin hydration catalyst of improved crush strength and microporosity comprised of aqueous phsophoric acid supported on a partly microporous silica xerogel which has been treated with steam under certain specific conditions.

DESCRIPTION OF THE PREFERRED EMBODIMENTS

In accordance with the preferred embodiment of the present invention, a substantially microporous silica xerogel of improved crush strength is first prepared and then is impregnated with phosphoric acid for use as a fixed bed vapor phase olefin hydration catalyst. While total acid saturation of the pores produces a workable catalyst, incomplete saturation is desirable. As noted above, xerogels can be produced as strong, hard masses or as extremely light, friable gels. Only the former is suitable for the catalyst of this invention.

Accordingly, the silica gel used to prepare the catalyst of this invention must be an intermediate density silica xerogel which is relatively inert to aqueous $H_3PO_4$ and characterized by the following properties:

| | |
|---|---|
| Particle size: | passes through 3 mesh and retained on 20 mesh, preferably retained on 12 mesh (U.S. Standard Sieve Series) |
| Bulk density: | 0.38–0.48 g/cc, preferably 0.40–0.45 |
| Pore volume: | 0.80–2.2 ml/g, preferably 0.85–1.3; with most ( about 90%) of the total pore volume being contributed by micropores having an average pore diameter (determined by the mercury porosimeter) of 100–200 Å |
| BET surface area: | 200–500 m²/g |
| Chemical composition: | $SiO_2$ >99w% (dry basis) $Fe_2O_3$ 0.01–0.03w% (dry basis) $Na_2O$ 0.02–0.09w% (dry basis) $Al_2O_3$ <0.42% (dry basis) |
| Crush strength (dry) of 50 particles: | not less than 1 pound |

The average crush strength determined on the compositions of the present invention are ascertained with a Chatillon Pellet Strength Tester which measures the minimum force necessary to just crush a particle between parallel plates. Such average crush strengths may be determined on (1) the dry xerogel, hereafter called "dry" crush strength; (2) the $H_3PO_4$ impregnated xerogel before drying, hereafter referred to as "wet with $H_3PO_4$" crush strength; and (3) the dry $H_3PO_4$ impregnated xerogel wet with water, hereafter referred to as "wet with water" crush strength. The average crush strength of the stream treated silica gel of this invention, after impregnation with aqueous phosphoric acid, wet or dry, will be substantially greater (usually about 70% or more) than a similarly impregnated but untreated gel, and with a much lower proportion of the gel particles having a crush strength of 2 pounds or less.

Suitable silica xerogels are commercially available. Examples include grade 57 intermediate density (ID) silica gel manufactured by Davison Chemical Company, Division of W. R. Grace & Co., Baltimore, Md., and 3–12 mesh intermediate density silica gel manufactured by Eagle Chemical Co., Mobile, Ala.

The granular silica xerogel is placed into a reactor, which is equipped with inlet and outlet lines, through a loading port which is then sealed. The xerogel is exposed to water vapor as it is heated under pressure until the treatment temperature is reached at both the inlet and outlet zones of the reactor. Heating can be accomplished by heating the reactor or by passing a hot flowing inert gas, optionally containing water vapor, through the xerogel bed in the reactor. It is important, however, that no liquid water be present.

Once the appropriate temperature and pressure conditions are attained, the gel is steam treated in an atmosphere having the appropriate relative humidity for a period of time called "hold time" which generally ranges from 4–16 hours. The relative humidity generally ranges from about 30% to about 100% at the treatment temperature. Total pressure employed is generally in the range of 20 to 1500 psig and preferably about 150–650 psig. The treatment temperature is above 100° C. and care is taken not to allow the temperature to attain a level of 200° C. or above. Preferably the temperature is about 145°–175° C. It has been observed that an increase in relative humidity or in hold time, or both, tends to increase "wet with $H_3PO_4$ crush strength" but also tends to lower the proportion of pore volume contributed by micropores; at the preferred treatment temperatures, the preferred relative humidity is about 30–50% and the preferred hold time is about 4–10 hours. After treatment, the xerogel is allowed to cool to ambient temperature. Cooling may be accelerated by circulation of a cool moist inert gas to avoid dehydration of the gel, yet not allow liquid water condensation on the gel. Ethylene or nitrogen is satisfactory as the cooling gas. After the gel has been cooled, the reactor is depressurized to atmospheric pressure.

Alternatively, the silica xerogel can be charged into a pressure vessel which is then pressurized with an inert gas. The xerogel is then heated while water in the vapor state only is allowed to admix with the inert gas which surrounds the gel. The inert gas is kept saturated with water vapor. This may be accomplished, for example, by initially charging liquid water into the vessel while keeping it separate and out of contact with the xerogel. The reactor is then closed, pressurized and heated externally. In this case, the liquid water is also heated and caused to vaporize, saturating the gas blanket with water vapor at all temperatures. Alternatively, the amount of water can be limited so as to be fully vaporized and give the desired relative humidity at treatment temperature. At the end of the treatment, the vessel is depressurized at the treatment temperature and swept with cool, moist inert gas to cool to ambient temperature without dehydration of the xerogel yet now allowing liquid water condensation on the gel.

The resulting xerogel is characterized by having an increased crush strength while retaining a substantial proportion of its microporosity.

After the water vapor treatment, the xerogel is impregnated with the phosphoric acid. This can be accomplished by charging the xerogel into a vessel containing aqueous phosphoric acid or by charging phosphoric acid into a vessel containing the gel, as desired. In either event, enough acid is used to cover the gel which is allowed to soak therein for an appropriate length of time after which the acid is allowed to drain off. The soaking process can be repeated one or more times as desired. Alternatively, the $H_3PO_4$ solution may be sprayed into the xerogel for a period of time using very small drop size, 0.001–0.005 mm, until the xerogel is saturated. The impregnated gel is then dried in any suitable manner such as by contact with heated circulating inert gas at elevated temperature to yield the catalyst.

The phosphoric acid used to impregnate the xerogel is employed as an aqueous solution in which the acid concentration is in the range of 40%–70%, and preferably in the range of 55%–60%. It has been found that about 210–250 pounds of 55% acid are convenient for each three cubic feet of steamed xerogel. The impregnation temperature can be in the range of 20° C. up to the boiling point of the acid solution but is preferably in the range of 25°–50° C. The gel is usually allowed to soak in the acid for 15 minutes to 4 hours, and preferably for 30–60 minutes. A longer time can be used if desired but is generally unnecessary. The excess liquid acid is usually allowed to drain off for 0.5–2 hours. The aqueous solvent for the phosphoric acid can optionally contain ethanol and/or a small percentage of a wetting agent such as polyoxyethylene to assist in filling the smaller micropores of the gel with acid.

The drying of the impregnated gel is preferably done under flow of a suitable gas such as nitrogen or ethylene with heat supplied either externally to the reactor or by preheating the gas. When the outlet temperature reaches about 120° C., the temperature is maintained until the impregnated xerogel is dry. This can be for about 15 minutes to 5 hours for laboratory scale samples and longer for plant scale depending on the quantity of impregnated xerogel being dried and geometry of the drying vessel. The drying of the gel is also preferably carried out under pressure. A pressure of 15–1500 psig is generally suitable with about 300–600 psig being especially desirable.

The supported catalyst of the present invention is used to hydrate olefins into alcohols. The catalyst can be used in any of the known processes and is particularly useful in the conversion of monoolefins of 2–10 carbon atoms such as ethylene, propylene and butylene. It is particularly useful in the ethylene hydration to ethanol and diethyl ether. The hydration reaction generally comprises bringing a gaseous mixture of olefin and water into continuous contact with the catalyst at elevated temperatures and pressures. This process, per se, is well known in the art and need not be described in any more detail here.

In the preferred ethylene hydration process, a reaction temperature of 235°–350° C., preferably 245°–300° C., a pressure of 500–1500 psig, preferably 900–1250 psig, a mol ratio of water to ethylene of 0.3–2.0, preferably 0.4–0.8, and a vapor velocity of 5–100 SCFM/ft$^3$ catalyst, preferably 15–45 SCFM/ft$^3$ [standard cubic feet per minute per cubic foot of catalyst; standard conditions being 1 atmosphere pressure at 60° F. (ca 25° C.) temperature] are used.

Electron micrographs of silica gel show that the physical structure can be described as a coherent aggregate of elementary particles of roughly spherical shape having a diameter of the order of 100 A. The elementary particle is an irregular three dimensional network of $SiO_4$ tetrahedra, each silicon atom being linked to four oxygens and each oxygen being linked to two silicons. At certain sites, the elementary particles may be linked together by Si-O-Si bridges. The particle surface is covered with hydroxyl groups which are responsible for the hydrophilic nature of normal silica gel.

The steaming process involves a vapor phase transport of matter resulting in the growth of large elementary particles at the expense of small ones, and resulting in the enlargement of the pores and loss in surface area. The transport of solid material during steaming results in the formation of fillets between the particles by deposition of the material in the regions of contact. Undoubtedly this contributes to the enhanced crush strength of the gel and the irreversible loss of microporosity and corresponding increase in macroporosity. Increased resistance to crushing could also be related to an additional mechanism involving the rearrangement of the elementary particles to form a more compact packing occurring as a response to stresses such as Van der Walls forces and to stresses caused from the shrinkage and sometimes disappearance of some of the smaller particles. The transport of material from a small elementary particle to a larger one is of molecular character. The silica gel skeleton is not affected during this process and, therefore, the pore volume does not change. The change not only results in the increased resistance to crushing of the dry xerogel granule but also of the xerogel granule impregnated with phosphoric acid solution.

At the lower temperatures and less drastic conditions of the instant process, as contrasted with the process described in German Offen. 2,237,015, only a portion of the pores are enlarged to the size of macropores (over 600 A). Wicke, Kolloidzeitschrift 86, 167 (1939) found, in studies of silica gel containing both micropores and macropores, that the surface area available in macropores is negligible in comparison with that in the micropores.

There is a loss of phosphoric acid from the catalyst during a hydration operation by a mechanism which is not known. One hypothesis is that a reaction between ethylene and phosphoric acid takes place in the pores to form a volatile but thermally unstable ethyl phosphate. A portion of this material volatilizes out of the pores before decomposing to phosphoric acid and ethylene or before its reaction with water to form alcohol and phosphoric acid. Thus, $H_3PO_4$ may be brought out of the pores. The same reaction may take place outside the pores, where the high linear gas velocity allows for a much more rapid movement before decomposition or reaction takes place. The process continues until the acid passes out of the reactor. It is believed that the diffusion of the ethyl phosphate out of the pores is more rapid with macropores than with micropores. This is based on evidence that in gas phase reaction over porous catalysts, Knudsen, or molecular flow, rules the rate of transport in the pores where there are micropores (in which the mean free path between intermolecular collisions of the gas molecules is greater than the pore diameter) whereas in macropores (where the magnitude of the mean free path and pore diameter are reversed) the more rapid ordinary diffusion predominates.

The advantages of micropores and macropores are suggested by Broekhoff (Chap. 1 of Physical and Chemical Aspects of Adsorbents and Catalysts, Linsen, Ed., Academedic Press, London (1970) as follows:

"Catalysts operate via the adsorption of molecules, and the surface area that is available for this adsorption is of major importance. This surface area is determined by the surface area in the micropores. Nevertheless, macropores play an important role in the operational use of these substances, since the rates of adsorption and the rates of the catalytic reactions depend largely on the rate of diffusion in the pores."

It will be recognized that the discussion above relates to the theory behind the invention. It has been set forth to assist in understanding the nature of this invention but I do not wish to be limited thereby. Whatever the reasons for the advantages obtained, it is clear that the catalyst and catalyst supports treated in accordance with this invention have substantially different physical characteristics, particularly with respect to micropore-macropore distribution and crush resistance, than the materials disclosed in German Offen. 2,237,015. As will be seen in Table I, a substantial proportion (19%-100%) of the total pore volume of the silica xerogel is contributed by micropores (average pore diameter 600 A. or less) when steaming is carried out in accordance with the invention but about 93% of the pore volume is in the form of macropores when temperatures in excess of 200° C. (392° F.) as suggested in the German Offen. are used.

Alternatively an improved fixed bed hydration catalyst with improved crush resistance and substantial microporosity can be obtained by subjecting the $H_3PO_4$ impregnated xerogel to the steaming process of this invention. However, the crush resistance is not as high as with the pre-acid impregnation steaming and the crush resistance in the initial stage of treatment is relatively low giving rise to a greater risk of catalyst breakup. For example, a sample of dry catalyst prepared from non-steamed xerogel was heated 4 hours at 163° C. and about 460 psig pressure and then cooled. The "dry" and "wet with water" crush strengths were 2.7 lbs. with 50% ≤ 2 lbs. and 1.2 lbs. with 86% ≤ 2 lbs., respectively. The water extracted dried support had a micropore volume of 1.03 cc/g indicating an insignificant loss in micropore volume.

There are two situations of what may be loosely termed "post-acid impregnation" steaming which would be distinguished from the present invention. For clarity, these will be referred to as "roasting" and "in situ steaming".

Roasting is described in British Pat. 1,306,141 and involves draining excess aqueous $H_3PO_4$ from the soaked silica gel, air drying for 3-24 hours, and thereafter oven drying for 1-4 hours, preferably 2 hours, at 100°-200° C., preferably 110° C., at atmospheric pressure. Since the purpose of this procedure is to dry the catalyst, the quantity of water vapor present (relative humidity) is generally low and becomes lower as drying continues. Additionally, the "hold time" at elevated temperature is shorter than that of the preferred pre-acid impregnation steaming procedure of this invention, and any post-impregnation steaming process requires a much longer hold time and/or higher temperature to produce roughly equivalent crush strength.

In situ steaming refers to the inherent post-acid impregnation steaming which takes place during the hydration reaction. The temperature and pressure conditions are appropriate; water vapor is present since it is a reactant; and the hold time is adequate since the reaction is run continuously. It takes, however, about 16 hours of in situ steaming of a roasted catalyst for the crush strength to approach that of a catalyst prepared by the preferred method of this invention which has not been subjected to in situ steaming (if so subjected, its crush strength would have further increased). Of course, if the pre-acid impregnation catalyst of this invention and a roasted catalyst are placed in service at the same time, the difference in crush strength will

TABLE I

| Original Gel. Total Pore Vol. cc/g | Steam Treatment Conditions | | | | Properties Steamed Xerogel | |
|---|---|---|---|---|---|---|
| | Temp. (° C.) | Hold Time (Hrs) | Pressure (psig) | Relative Humidity | Micropore Vol. cc/g | Micropore Vol. % of Original Total Pore Vol. |
| 1.08 | 150 | 16 | 1015 | 100 | 1.09 | 101 |
| 1.08 | 163 | 4 | 45 | 100 | 0.944 | 87 |
| 1.08 | 163 | 4 | 60 | 100 | 0.904 | 84 |
| 1.08 | 163 | 4 | 165 | 43 | 0.900 | 83 |
| 1.08 | 163 | 4 | 315 | 35 | 1.02 | 94 |
| 1.08 | 163 | 4 | 315 | 47 | 0.958 | 89 |
| 1.08 | 163 | 4 | 315 | 57 | 0.954 | 78 |
| 1.08 | 163 | 4 | 315 | 59 | 0.742 | 68 |
| 1.06 | 163 | 6 | 615 | 70 | 1.04 | 98 |
| 1.17 | 163 | 4 | 615 | 40 | 0.963 | 82 |
| 1.11 | 163 | 8 | 615 | 31 | 0.964 | 87 |
| 1.08 | 177 | 16 | 769 | 100 | 0.200 | 19 |
| 1.08 | 205 | 16 | 615 | 93 | 0.040 | 3.7 |
| 1.08 | 205 | 16 | 615 | 71 | 0.060 | 5.6 |
| 1.08 | 205 | 16 | 880 | 100 | 0.076 | 7.0 |
| 1.08 | 260 | 16 | 615 | 34 | 0.020 | 1.9 |
| 1.08 | 260 | 16 | 615 | 26 | 0.027 | 0.65 |
| 1.08 | 276 | 16 | 1015 | 43 | 0.029 | 2.7 |

All pore volume values in this specification are about ± 0.01 eventually become negligible. It also bears repeating that the most sensitive time for the xerogel is during acid impregnation.

The following Examples are set forth to further illustrate the invention but are not intended to limit it. Unless otherwise specified, throughout this specification and claims all parts and percentages are by weight.

EXAMPLE 1

A sample of 300 ml grade 57 ID silica gel granules, manufactured by Davison Chemical Company, and having properties described by them as follows: pore volume 1.04 cc/g; surface area 350 m$^2$/g; average pore diameter 120 A.; bulk density of about 27 lbs/ft$^3$; retained on 6 mesh; was selected for steam treatment. The gel was charged to a 0.75 inch OD (outer diameter) × 0.065 inch WT (wall thickness) × 30 inches long tubular reactor. The reactor was contained in a 2.5 inch OD × 0.065 WT heating jacket. Dowtherm was used for the liquid heating medium in the jacket and was heated by electric band heaters. The boiling temperature of the Dowtherm was controlled by adjusting the pressure (< 1 atm) on the jacket. The temperatures were monitored with thermocouples whose output were fed to a continuous temperature recorder. The gel thermocouple was located in the middle of the bed and no temperature excursions were observed. The pressure was measured on the dry air inlet feed line and controlled with a pressure control valve located on the reactor outlet.

The system was pressured to 300 psig with compressed air, at which time the bed was rapidly heated to 109° C. Water was then fed, via a Milton Roy instrument minipump, concurrently with air through an electrically heated vaporizer fitted with an internal thermocouple located at the reactor inlet. The water and air feed rates along with reactor temperatures were programmed to maintain a constant humidity of 35% until the final desired operating temperature of 163° C. was reached. The system was held for 4 hours at the final operating conditions of 300 psig pressure, 163° C. temperature and 35% relative humidity. At this point the water feed was discontinued and the heaters turned off. The gel was then allowed to cool to room temperature with compressed air flowing through the gel. The pressure was then released and the gel removed.

Olefin hydration catalysts were made from the steamed and non-steamed 57 ID silica gel granules by immersing them in 55% aqueous H$_3$PO$_4$ for 2 hours, draining for 1 hour and then oven drying them at 110°–120° C. for 2 hours.

The effect of steam treatment of the silica gel on its microporosity and average crush strength and the average crush strength of the catalyst is shown in Table II.

TABLE II

| | Unsteamed | Steamed |
|---|---|---|
| Measured Total Pore Volume, cc/g | 1.08 | 1.03 |
| Measured Micropore Volume, cc/g | 1.03 | 1.02 |
| Original crush strength prior to H$_3$PO$_4$ impregnation (dry) | 8.6 with 0% 2 lbs. | 9.3 with 0% 2 lbs. |
| Crush strength, wet with H$_3$PO$_4$ | 2.6 with 50% 2 lbs. | 4.6 with 16% 2 lbs. |
| Crush strength after impregnation (dry) | 2.7 with 50% 2 lbs. | 6.1 with 10% 2 lbs. |
| Crush strength, wet with water (after H$_3$PO$_4$ impregnation | 1.2 with 86% 2 lbs. | 2.6 with 50% 2 lbs. |

TABLE II-continued

| | Unsteamed | Steamed |
|---|---|---|
| and drying) | | |

The foregoing Table II illustrates an important aspect of this invention. The most critical time during normal hydration operation is during start-up because this is when pressure and gas flow are first applied. At this time, the catalyst is at its weakest and is most liable to crumble. The data shows that the average crush strength (dry after impregnation) of the unsteamed gel has dropped 70% of its original value while the steamed gel dropped about 50%. Of even greater importance, half of the unsteamed gel has a crush strength of 2 pounds or less at this point while only 16% of the steamed gel is 2 pounds or less. There is always a danger of upset or water condensation during the hydration process and if this occurs, the crush strength of the supported catalyst will degenerate still further. This is the significance of the "wet with water" values set out, and it will be observed that the unsteamed gel has a strength prohibitive for fixed bed operations while the steamed gel is still satisfactory.

It is interesting to note that the crush strength of the unsteamed acid impregnated gel remained essentially the same when that gel was dried while with the steamed gel, the average strength increased and the amount of granules of 2 pounds or less decreased.

EXAMPLE 2

A sample of 600 ml of grade 57 ID silica gel granules, manufactured by Davison Chemical Co., and having properties described by them as follows: pore volume 1.04 cc/g; surface area 350 m$^2$/g; average pore diameter 120 A.; bulk density of about 27 lbs/ft$^3$; retained on 6 mesh; was selected for steam treatment. The gel was poured into a cylindrical Pyrex glass liner which was then, in turn, placed into a stainless steel pressure vessel. The design operation conditions for the pressure vessel were pressures to 1000 psig and temperatures to 600° F. (ca 315° C.). The free volume with gel loaded was 495 ml.

After placing the glass liner charged with silica gel into the pressure vessel, an excess of liquid water (5.66 ml) was pipetted into the vessel but outside the liner. The pressure vessel was closed and sealed and pressurized to 450 psig (25° C.) with nitrogen from a pressure cylinder through a valve, which was then closed and disconnected from the pressure cylinder. The pressure vessel with valve was completely immersed in a fluidized sand bath preheated to 300° F. (ca 150° C.). The gel was thus surrounded by nitrogen having a relative humidity of 100%. The total pressure was 705 psig. Treatment was continued for 16 hours after which the reactor was removed from the bath, vented to atmosphere pressure while still hot and then cooled. The effect of this treatment on the gel properties is shown in Table III.

TABLE III

| Treatment | Total Pore Volume, cc/g | % Micropores ( ≤ 600 A pore diameter) |
|---|---|---|
| Non-steamed | 1.08 | 95.4 |
| Steamed | 1.09 | 99.7 |

The steam treatment did not appreciably alter the micropore volume. However, an even greater effect of the treatment is shown by the crush strength of catalysts made from the treated gel as compared to the untreated gel.

Olefin hydration catalysts were made from the steamed and non-steamed 57 ID silica gel granules by immersing them in 55% aqueous $H_3PO_4$ for 2 hours, draining for 1 hour and then oven drying them at 110°–120° C. for 2 hours. The properties of these catalysts are shown in Table IV.

TABLE IV

| Treatment | Free $H_3PO_4$ lbs/ft$^3$ | Crush Strength, lbs | | | | | |
|---|---|---|---|---|---|---|---|
| | | Dry | | | Wet With Water | | |
| | | Av. | % | ≤2 lbs | Av. | % | ≤2 lbs |
| Non-steamed | 21.05 | 2.7 | 50 | | 1.2 | 86 | |
| Steamed | 21.19 | 9.8 | 4 | | 4.5 | 24 | |

Catalysts from the non-steamed gel had lost "wet with water" crush strength to a prohibitive degree for fixed bed operation in the event that water condensation occurs during an upset in operating conditions. On the other hand, an accidental wetting of the catalyst from steamed gel with liquid water will not ruin it since its average crush strength wet is still 4.5 pounds.

This improved catalyst is especially useful in the continuous fixed bed vapor phase hydration of olefins to the corresponding alcohols and ethers.

EXAMPLE 3

300 ml (262 g) of an olefin hydration catalyst of this invention was prepared as described in Example 2 and charged into a steel jacketed reactor. The reactor was then sealed and hot oil at 264° C. was circulated through the jacket to heat the catalyst. When the temperature of the bed reached 236° C., a mixture of ethylene and water in a mol ratio of water to ethylene of 0.58 was passed down through the bed at a vapor velocity of 29.2 SCFM/ft$^3$ catalyst and at a pressure of 1000 psig. Reacted effluent gas was passed through a pneumatically operated valve which controlled reaction pressure and through which the effluent gas pressure was reduced to atmospheric.

As the reaction took place, a steady state was attained in which the bed temperatures near the top and bottom of the bed was 270° C. and 281° C., respectively, and the pressure was 1000 psig. For purposes of measuring catalyst activity under steady state conditions, effluent gas was diverted through a special route for exactly 1 hour for data collection. The effluent gas was cooled in a condenser using 20° C. water coolant and a liquid phase condensed comprised of the bulk of the alcohol synthesized along with water. Non-condensed gas was then passed through a washing tower in which liquid methanol was trickled down through the column countercurrent to the gas stream to wash out the ethanol and ether. These components were measured in the methanol wash by gas-liquid chromatography and were also recovered by distillation. It was found that the space time yield of alcohol and ether were 1.26 and 0.41 gallons (at 20° C.) per cubic foot catalyst per hour, respectively. The conversion of ethylene to ethanol was 6.17% and of ethylene to ether was 2.29%.

EXAMPLE 4

Preparation of the steamed silica xerogel described in Example 2 was repeated except that the volume of liquid water charged was 6.26 ml, the initial pressure was 421 psig and the temperature of the sand bath was 350° F. (ca 177° C.). The time was 16 hours. The relative humidity in this case was 100% and the total pressure was about 770 psig. The resulting gel had a total pore volume of 1.05 cc/g, 19% micropores < 600 Å. pore diameter), an average crush strength of 5.7 pounds and 10% had a crush strength of 2 pounds or less.

Catalyst was made from this gel by phosphoric acid impregnation following the precedure and conditions set forth in Example 1. The resulting catalyst had an average dry crush strength of 6.9 pounds, 4% had a crush strength ≤ 2 pounds, and a "wet with water" crush strength of 5.6 pounds with 10% ≤ 2 pounds. The acid content was 22.72 pounds $H_3PO_4$/ft$^3$ catalyst. This improved catalyst is especially useful in the continuous fixed bed vapor phase hydration of olefins to the corresponding alcohol and ethers.

EXAMPLE 5

Example 3 was repeated using the catalyst of Example 4, a mol ratio of water to ethylene in feed of 0.56, a vapor velocity of 28.09 SCFM/ft$^3$ catalyst, a heating oil temperature of 266° C. and a reaction pressure of 1000 psig. The bed temperatures near the top and bottom of the vessel were 261° and 282° C., respectively. The space time yields of ethanol and ether were 1.18 and 0.51 gallons/ft$^3$ catalyst/hour, respectively. The conversion of ethylene to alcohol was 5.92% and of ethylene to ether was 2.89%.

EXAMPLE 6

Approximately 3000 ft.$^3$ of Davison Grade 57 ID silica xerogel having measured properties as follows:

| | |
|---|---|
| Total Pore Volume | 1.11 cc/g |
| Micropore Volume | 1.03 cc/g |
| "Wet with $H_3PO_4$ Crush Strength" | 1.7 lbs. with 78% ≤ 2 lbs. |
| Surface Area (BET) | 285 m$^2$/g | were charged to an adiabatic reactor. The reactor was pressured to 600 psig and held there using ethylene. The xerogel was then heated to about 325° F. (163° C.) for approximately 11 hours with preheated recycled ethylene flowing at a rate of about 50,000 SCFM. Water was introduced into the gas stream when the bed temperature reached about 200° F. (93° C.) so as to provide about 30% relative humidity in the gas during the heat up (about 4 hours) and hold time periods. The hold time at 325° F. (163° C.) and about 30% relative humidity [equivalent to gas saturation at about 250° F. (121° C.)] and 600 psig was 6 hours, at which point was water feed was stopped and the bed cooled with ethylene gas to about 50° C. after which the reactor was depressurized.

Samples of the resulting steamed silica xerogel taken from the top and bottom of the bed had the following properties:

| | | |
|---|---|---|
| Total Pore Volume (Water Titration) | | 1.05 cc/g |
| Micropore Volume | | 0.964 cc/g |
| Average "Wet with $H_3PO_4$" Crush Strength | (Top of bed) | 4.1 lbs. with 22% ≤ 2 lbs. |
| | (Bottom of bed) | 4.5 lbs. with 12% ≤ 2 lbs. |
| Mesh Size | | retained on 6 mesh |

The percent micropore volume based on the original total pore volume was about 87%; thus substantial micropore volume was retained. The average "wet with $H_3PO_4$" crush strength increased from 1.7 lbs. to 4.2 lbs.

EXAMPLE 7

The steam treated xerogel prepared in situ in Example 6 was made into a catalyst in situ and used in continuous vapor phase process for the hydration of ethylene to ethanol and ether as follows:

55% aqueous $H_3PO_4$ was pumped into the reactor until the steam treated xerogel was completely immersed. After two hours, the acid was drained off. The reactor was closed and start up of the hydration commenced using preheated and recycled ethylene and water vapor in an approximate ratio so as to achieve a dry catalyst throughout the hydration. Ultimately by virtue of preheated feed gas and heat of reaction, the bed reached a steady final inlet temperature of about 260° C. and a pressure of about 900 psig. The effluent gaseous reaction mixture was cooled under pressure and the resultant liquid mixture separated in a high pressure separator. The vapor stream from the separator was sent to an alcohol scrubber where alcohol was washed out with water and washed gas was sent to a recycle compressor and, after purging a small stream, was returned to the reactor. The wash solution was combined with the liquid phase from the high pressure separator and fed into an ether stripper column where ether and other like components were removed, sent to an off-gas compressor, the recycle compressor and ultimately recycled to the reactor.

The dilute alcohol solution from the bottom of the ether stripper was concentrated in a pre-rectifier column and then catalytically hydrogenated to convert by-product carbonyl groups to alcohol groups and saturate by-product unsaturated compounds for easy removal via distillation. Pre-rectifier column bottom were recycled to the alcohol scrubber column since these are essentially water. After hydrogenation, the alcohol was further purified by extractive distillation and rectified to continuously yield a high purity alcohol product. 55% aqueous $H_3PO_4$ solution was added to the bed at the top to replace acid.

EXAMPLE 8

A sample of 600 ml of Eagle Chemical Co. 3–12 mesh intermediate density silica gel granules having the following properties:

| | |
|---|---|
| BET Pore volume: | 1.02 cc/g |
| BET Surface area: | 270 m²/g |
| Bulk density: | 0.40 g/ml (25 lb/ft³) |
| "Wet with $H_3PO_4$" Crush Strength | 1.6 lbs. with 86% ≤2 lbs. | was selected for steam treatment using the same apparatus as described in Example 2 for steam treating. Conditions for steam treatment were 325° F. (ca 163° C.) for 16 hours at 600 psig with nitrogen saturated with water vapor at 300° F. (ca 149° C.). Relative humidity was 70%.

350 ml (142 g) of the steam treated gel were immersed in 55% aqueous $H_3PO_4$ for 2 hours, drained 1 hour and oven dried at 110° C. for 2 hours. The steam treated impregnated gel had an average "wet with $H_3PO_4$" crush strength of 5.6 pounds with 20% ≤ 2.0 pounds and a dry crush strength of 6.5 pounds with 14% ≤ 2.0 pounds. In contrast, catalyst prepared from unsteamed gel had an average "wet with $H_3PO_4$" crush strength of less than 2 pounds.

The final weight of the catalyst was 172.6 g. Water extraction of this catalyst left a support with a substantial micropore volume.

300 ml of the catalyst prepared from this steam treated gel were charged to the olefin hydration reactor described in Example 3 and used in the fixed bed continuous catalytic hydration of propylene with water to isopropanol and diisopropyl ether.

After charging catalyst and sealing the reactor, hot oil at 202° C. was circulated through the jacket to heat the catalyst. When the temperature of the bed reached 200° C., a mixture of propylene and water in a mol. ratio of water to propylene of 0.65 was passed down through the bed at a vapor velocity of 47 SCFM/ft³ catalyst, at a pressure of 370 psig. Reacted effluent gas passed through a pneumatically operated valve which controlled reaction pressure and through which effluent gas pressure was reduced to atmospheric. Phosphoric acid was continuously replaced at its loss rate using a dilute solution added at the top of the bed as a spray.

As reaction took place, a steady state was attained in which bed temperature near the top and bottom of the bed were 198° C. and 210° C., respectively, and pressure was 370 psi. For purposes of measuring catalyst activity under steady state conditions, effluent gas was diverted through a special route for exactly one hour for data collection. The effluent gas was cooled in a condenser using 20° C. water coolant and a liquid phase condensed which was comprised of the bulk of the alcohol synthesized along with water. Non-condensed gas was then passed through a washing tower to which liquid methanol was trickled down the column countercurrent to the gas stream to wash out the isopropanol and isopropyl ether. These components were measured in the methanol wash by gas-liquid chromatography and were also recovered by distillation. The effluent propylene volume was measured. The isopropanol and isopropyl ether content of the condensed aqueous phase was also measured by gas chromatographic analysis, then recovered by distillation. The results after 3 hours were as follows: the space time yield of isopropyl alcohol was 2.36 gallons (at 20° C.)/ft³ catalyst/hour. The conversions of propylene to isopropanol and isopropyl ether were 5.72% and .009%, respectively.

EXAMPLE 9

300 ml of fixed bed catalyst prepared as in Example 8 were used in the same system as Example 8 to continuously hydrate ethylene with water to ethanol and diethyl ether. The free $H_3PO_4$ content was 22.57 lbs/ft$^3$. Under conditions of top and bottom bed temperature, mol ratio water to ethylene, vapor velocity and reaction pressure of 253° C. and 277° C., 0.49, 33 SCFM/ft$^3$ catalyst and 1000 psi, the conversion of ethylene to ethanol and to diethyl ether was 5.00% and 1.50%, respectively, and the space time yields of alcohol and ether were 1.23 and 0.33 gallons (at 20° C.)/ft$^3$ catalyst/hour, respectively.

EXAMPLE 10

150 ml of Davison grade 57 ID silica gel having total pore and micropore volumes of 1.08 cc/g and 1.03 cc/g and an average "wet with phosphoric acid" crush strength of 2.6 lbs. with 50% equal to or less than 2 lbs. were charged to a reactor consisting of a stainless steel tube 0.75 inch O.D. × 0.065 inch W.T. × 30 inches long. The reactor was contained in a 2.5 inch OD × 0.065 inch wall thickness heating jacket. Dowtherm was used for the liquid heating medium which is heated by electric band heaters on the jacket. The boiling temperature of the Dowtherm is controlled by adjusting the pressure (< 1 atm.) on the jacket.

The temperature of the gel was monitored with thermocouples whose output were fed to a continuous temperature recorder. The thermocouples were located in the center of the gel bed and no temperature excursions were observed.

The conditions for steaming the gel were 30 psig, 325° F. (163° C.), 100% relative humidity, and 8 hour hold period.

The experimental procedure involved pumping water with a DCL pump through a series of vaporizers and downflow through the gel contained in the lower half of the reactor tube. The vaporizers were always maintained at a higher temperature than the bed to insure complete vaporization of the water. The reactor effluent steam was vented to the atmosphere.

After charging the gel (150 ml) to the reactor, the vaporizers and bed were brought to the 180° C. and 163° C., respectively, which took approximately one hour.

The pressure was measured on the water feed line and controlled with a pressure control valve located at the reactor outlet. Water feed (43 ml/hr) was started when the vaporizer and bed temperatures were obtained, and the eight hour treatment period was started when the system was in the range 22 to 31 psig pressure. When the steam was observed in the reactor effluent, the operating conditions were held for four hours. The water feed and all heaters were turned off after the four-hour treatment. The gel was then allowed to cool to room temperature with a dry nitrogen purge. The treatment did not affect particle size (retained on 6 mesh). The micropore volume of the steamed gel was 0.813 cc/g representing 75% of the original total pore volume. The average "wet with phosphoric acid" crush strength was 4.9 lbs. with 14% ≤ 2 lbs., substantially greater than that of the non-steamed gel (2.6 lbs. with 50% ≤ 2 lbs.).

EXAMPLE 11

300 ml of untreated gel from the same lot as that used in Example 10 was steamed at 300 psig and 325° F. (163° C.) at 47% relative humidity for a hold time of 4 hours as follows.

The apparatus used in Example 10 was modified by replacing the DCL pump with a Milton Roy Instrument minipump for pumping water. It was further modified by replacing the reactor with a larger one measuring 0.96 inch O.D., 0.065 inch wall thickness and 27.6 inches high. Air from a pressurized cylinder was passed through a rotometer then through the bed at 500 SCFM/ft$^3$ gel.

After pressurizing the system to 300 psig with air, the bed temperature was increased to 325° F. (163° C.) at which time the water feed and temperature were both increased manually until the final operating conditions were attained. The water feed rates were 5.3 cc/hr in the first hour as bed temperature rose from 100° to 121° C., 8.9 cc/hr in the second hour as bed temperature rose from 121° C. to 141° C., and 16.3 cc/hr in the third hour as bed temperature rose from 141° C. to 163° C. Thereafter the rate was 18.3 cc/hr for four hours as the bed temperature remained at 163° C. Following the four-hour treatment, the water feed pump and all heaters were turned off. The gel was then allowed to cool to room temperature under flowing dry air. The particle size (retained on 6 mesh) was unaffected by the treatment.

The micropore volume of the steamed gel was 0.958 cc/g representing 89% of the original total pore volume. The "wet with phosphoric acid" crush strength was 4.7 with 4% less than or equal to 2 lbs. compared to 2.6 lbs. and 50% ≤ 2 lbs. for the non-steamed gel.

EXAMPLE 12

A 350 cc sample (146.2 g) of the steamed gel of Example 6 was impregnated with phosphoric acid, drained (wet weight 376 g) then dried in an oven at 120° C. to yield an olefin hydration catalyst having the following characteristics:

| | |
|---|---|
| dry crush strength | 6.1 lbs. with 8% ≤ 2 lbs. |
| "wet with water crush strength" | 3.6 lbs. with 32% ≤ 2 lbs. |
| Free $H_3PO_4$ (as 100% acid) | 21.46 lbs./ft$^3$ catalyst |
| Mesh size | retained on 6 |

300 ml (257.8 g) of the catalyst were charged to the reactor described in Example 3, and the same general hydration procedure was followed except that the following conditions were employed:

mole ratio feed water/ethylene 0.54
vapor velocity 34.85 SCFM/ft$^3$ catalyst
top and bottom bed temperature 260° C. and 287° C. respectively The resulting space time yield of alcohol and ether in gallons (20° C.) per ft$^3$ catalyst per hour were 1.50 and 0.796 respectively. The conversion of ethylene to alcohol and ether were 6.01% and 3.58% respectively.

Various changes and modifications can be made in the process and products of this invention without departing from the spirit and the scope thereof. For example, while the catalyst of this invention has been described with respect to fixed bed use, it can also be used in a moving bed. The various embodiments disclosed herein were set forth for the purpose of illustration and were not intended to limit the invention.

I claim:

1. In a process for hydrating olefins to the corresponding alcohols by contacting the olefin and water vapor with a catalyst at elevated temperatures and pressures, the improvement which comprises employing as the catalyst, a preformed $H_3PO_4$ impregnated, water vapor treated silica xerogel, wherein said xerogel has a particle size passing through 3 mesh and retained on 20 mesh, a bulk density of 0.38–0.48 g/cc, a pore volume of 0.80–2.2 ml/g, a BET surface area in the range of 200–500 m²/g and the following chemical composition in terms of weight percent dry basis: $SiO_2$ over 99%, $Fe_2O_3$ 0.01–0.03%; $Na_2O$ 0.02–0.09%; and $Al_2O_3$ less than 0.4%, said xerogel having been contacted with water vapor at a temperature above 100° C. and less than 200° C., a relative humidity of about 30–100%, and a total pressure of 20–1500 psig.

2. The process of claim 1 wherein said water vapor treatment was effected prior to impregnating the xerogel with $H_3O_4$.

3. The process of claim 2 wherein said xerogel was contacted with said water vapor for 4–16 hours.

4. The process of claim 3 wherein said temperature was 145°–175° C., said relative humidity was about 30%–50%, said total pressure was about 150–650 psig, and said contact time was about 4–10 hours.

5. The process of claim 1 wherein said particle size is retained on 12 mesh, said bulk density is 0.40–0.45 g/cc, and said pore volume is 0.85–1.3 ml/g.

6. The process of claim 2 wherein said olefin is ethylene or propylene.

7. The process of claim 2 wherein said olefin is ethylene.

8. The process of claim 1 wherein said xerogel was contacted with water vapor after it is impregnated with $H_3PO_4$.

9. The process of claim 8 wherein said olefin is ethylene.

* * * * *